United States Patent [19]

Novick et al.

[11] Patent Number: 5,621,077
[45] Date of Patent: Apr. 15, 1997

[54] SOLUBLE IFN-β2/IL-6 BINDING PROTEIN ITS PREPARATION, AND PHARMACEUTICAL COMPOSITIONS CONTAINING IT

[75] Inventors: Daniela Novick, Rehovot; Louise Chen, Ramat Aviv, both of Israel; Hartmut Engelmann, Munich, Germany; Michel Revel, Rehovot, Israel; Menachem Rubinstein, Givat Shmuel, Israel; David Wallach, Rehovot, Israel

[73] Assignee: Yeda Research and Development Co. Ltd., Rehovot, Israel

[21] Appl. No.: 329,785

[22] Filed: Oct. 27, 1994

Related U.S. Application Data

[60] Continuation of Ser. No. 43,976, Apr. 7, 1993, abandoned, which is a division of Ser. No. 530,580, May 30, 1990, Pat. No. 5,216,128.

[30] Foreign Application Priority Data

Jun. 1, 1989 [IL] Israel ......................... 090488
Nov. 26, 1989 [IL] Israel ......................... 092444

[51] Int. Cl.$^6$ ................................. C07K 14/705
[52] U.S. Cl. ................... 530/350; 435/64.1; 530/388.22
[58] Field of Search ................. 435/69.1; 530/350, 530/388.22; 514/2, 12, 21

[56] References Cited

U.S. PATENT DOCUMENTS

| | | | |
|---|---|---|---|
| 4,289,690 | 9/1981 | Pestka et al. | 530/351 |
| 4,485,017 | 11/1985 | Tan et al. | 210/635 |
| 4,578,335 | 3/1986 | Urdal et al. | 435/70.4 |
| 4,771,125 | 9/1988 | Schnaper et al. | 530/351 |
| 4,894,330 | 1/1990 | Hershenson et al. | 435/69.51 |
| 4,973,577 | 11/1990 | Vale, Jr. et al. | 514/12 |
| 5,030,576 | 7/1991 | Dull et al. | 435/69.7 |

FOREIGN PATENT DOCUMENTS

28720/89 7/1989 Australia.
0325474 7/1989 European Pat. Off..

OTHER PUBLICATIONS

Smith et al, Science 238: 1704–1707, 18 Dec. 1987.
Weber et al. 1988 J. of Chromatography 431: 55–63.
Hirata, Y. et al.: "Characterization of IL–6 receptor expression by monoclonal and polyclonal antibodies", *The Journal Of Immunology*, vol. 143, No. 9, Nov. 1, 1989, The American Association of Immunologists, pp. 2900–2906.
Patent Abstracts of Japan, vol. 13, No. 388, (C–630) [3736], Aug. 28, 1989; & JP–A–1137992 (Chuzo Kishimoto), May 3, 1989 & Chemical Abstracts, vol. 112 1990, p. 586, abstract No. 156727j.
Novick D. et al, "Purification of soluble cytokine receptors from normal human urine by ligand–affinity and immunoaffinity chromatography", J. Chromatog., vol. 510 (1990), pp. 331–337.
Yamasaki, K. et al "Cloning and Expression of the Human Interleukin-6 (BSF–2/IFN β2) Receptor", Science, vol. 241, Reports, 2 Aug. 1988, pp. 825–828.
Novick, D. et al "Soluble Cytokine Receptors Are Present in Normal Human Urine", J. Exp. Med., vol. 170, Oct. 1989, pp. 1409–1414.
Novick, D. et al "Monoclonal Antibodies for Affinity Purification of IL–6/IFN–β2) and for Neutralization of HGF Activity", Hybridoma, vol. 8, No. 5, 1989, pp. 561–567.
Revel, M. et al "Biological Activities of Recombinant Human IFN–β2/IL–6 (*E. coli*)", Ann. N.Y. Acad. Sci., vol. 557, Jun. 15, 1989, pp. 144–156.
Taga, T. et al "Interleukin–6 Triggers the Association of Its Receptor with a Possible Signal Transducer, bp130", Cell, vol. 58, Aug. 11, 1989, pp. 573–581.

*Primary Examiner*—John Ulm
*Attorney, Agent, or Firm*—Browdy and Neimark

[57] ABSTRACT

Human natural IFN-β2/IL-6 receptor and its soluble extracellular fragment are provided in substantially purified form and are shown to stimulate and to enhance beneficial effects of IFN-β2/IL-6, such as its antiproliferative activity. Polyclonal and monoclonal antibodies raised against the soluble fragment of the receptor are also provided.

2 Claims, 3 Drawing Sheets

SOLUBLE IFN-β2/IL-6 BINDING PROTEIN ITS PREPARATION, AND PHARMACEUTICAL COMPOSITIONS CONTAINING IT

CROSS-REFERENCE TO RELATED APPLICATIONS

This application is a continuation of Ser. No. 08/043,976, filed Apr. 7, 1993, now abandoned, which is a division of co-pending parent application Ser. No. 07/530,580, filed May 30, 1990, now U.S. Pat. No. 5,216,128.

FIELD OF THE INVENTION

This invention relates to substantially purified human Interferon-β2/ Interleukin-6 Receptor (hereinafter IFN-β2/IL-6-R), its soluble extracellular fragment, salts, functional derivatives, precursors and active fractions thereof. The invention also relates to a process for the purification of human natural IFN-β2/IL-6-R and its soluble extracellular fragment, to the cloning of the soluble extracellular fragment and its production by recombinant DNA techniques, and to polyclonal and monoclonal antibodies raised thereto. It further relates to pharmaceutical compositions comprising human natural IFN-β2/IL-6-R or its soluble extracellular fragment, or salts, functional derivatives, precursors and active fractions thereof.

BACKGROUND OF THE INVENTION

Interferon-β2, now designated Interleukin-6 (hereinafter IFN-β2/IL-6), is a multifunctional cytokine that regulates the growth and differentiation of various cells and tissues and appears to be one of the important mediators of the response to viral and bacterial infections and to shock. The biological effects now associated with IFN-β2/IL-6 include: stimulation of immunoglobulin secretion by mature B lymphocytes (BSF-2 activity), growth stimulation of plasmacytomas and hybridomas (HGF activity), activation of T cells, stimulation of hepatic acute phase protein synthesis (HSF activity), stimulation of hematopoiesis, cell differentiation (DIF activity), inhibition of tumor cell growth (AP activity) and other IFN-like effects. As a typical cytokine, IFN-β2/IL-6 is secreted by many cell types and acts in various combinations with other interleukins and interferons. Among its activities viewed as having antitumor potential are: inhibition of cancer cell growth and colony formation, differentiation of malignant cells to more normal phenotypes, stimulation of normal hematopoiesis, stimulation of T-lymphocyte activation, stimulation of antibody secretion by B-cells, stimulation of complement synthesis, and stimulation of antiprotease synthesis.

The cloning of the human IFN-β2/IL-6 receptor was reported (Yamasaki, et al., Science, Vol. 241, pp. 825–828(1988)). However, the natural human IFN-β2/IL-6 receptor and a soluble extracellular fragment thereof have not been isolated and described in the literature.

SUMMARY OF THE INVENTION

It has now been discovered that the IFN-β2/IL-6-R and a soluble fragment thereof strongly enhance the stimulatory effect of IFN-β2/IL-6 on mouse plasmacytoma cells and markedly enhance the growth inhibitory effect of human IFN-β2/IL-6 on human breast cancer cells and thus can be used to enhance the biological activity of IFN-β2/IL-6. Thus, the present invention provides human natural Interferon-β2/ Interleukin-6 Receptor, herein designated IFN-β2/IL-6-R, its soluble extracellular fragment, salts, functional derivatives, precursors and active fractions thereof, and mixtures of any of the foregoing, which specifically bind IFN-β2/IL-6 and can stimulate and enhance the beneficial biological effects of IFN-β2/IL-6.

The invention is directed to said human natural IFN-β2/IL-6-R in substantially purified form, being free of proteinaceous impurities, and to a process for its isolation.

The invention also relates to the human IFN-β2/IL-6-R soluble extracellular fragment in substantially purified form, being free of proteinaceous impurities and moving as a single peak on reversed-HPLC and to a process for the isolation and purification of said fragment from human fluids, e.g. urine.

The invention is also directed to polyclonal and monoclonal antibodies against the human IFB-822/IL-6-R and its soluble extracellular fragment.

The invention further concerns the production of the IFN-β2/IL-6-R soluble extracellular fragment by recombinant DNA techniques, including the preparation of DNA sequences coding for the IFN-β2/IL-6-R soluble extracellular fragment, or for a protein substantially homologous therewith, the construction of expression vehicles comprising them and of host cells transformed therewith, and to a process for producing IFN-β2/IL-6-R soluble extracellular fragment or a protein substantially homologous therewith, by culturing said transformant cells in a suitable culture medium.

The human natural IFN-β2/IL-6-R of the invention and its soluble extracellular fragment and salts, functional derivatives, precursors and active fractions thereof, and mixtures of any of the foregoing, are for use as active ingredients in combination with- IFN-β2/IL-6 of pharmaceutical compositions to enhance the beneficial effects of IFN-β2/IL-6.

DETAILED DESCRIPTION OF THE INVENTION

The receptors of IFN-β2/IL-6 on various human cells are identified by cross-linking experiments with radiolabelled IFN-β2/IL-6. Briefly pure IFN-β2/IL-6 is labelled with [$^{125}$I] by the chloramine-T method according to published procedures, retaining its intact biological activity. Such labelled IFN-β2/IL-6 is allowed to react with various human cells at 4° C. and the resulting IFN-β2/IL-6 receptor complexes are covalently cross-linked and then analyzed by polyacrylamide gel electrophoresis (PAGE) in the presence of sodium dodecyl sulfate (SDS) followed by autoradiography. After their identification, the receptors are isolated by a method which comprises solubilizing human cells bearing the receptors to obtain a suspension, centrifuging the suspension to obtain a supernatant, applying the supernatant to an immobilized IFN-β2/IL-6 or anti-IFN-β2/IL-6-R monoclonal antibody column, and eluting the bound receptor protein by varying pH conditions, in a state of enhanced purity. If necessary, the eluted fractions may be further purified.

The soluble extracellular fragment of IFN-β2/IL-6-R of the invention was found in human urine. In its substantially purified form, which is substantially free of proteinaceous impurities, it has a molecular weight of about 50 (40–60)K when analyzed by SDS PAGE under non-reducing conditions and it moves as a single peak on reversed-phase HPLC.

It is further characterized by the following sequence obtained by N-terminal sequence analysis of the protein:

Leu-Ala-Pro-Arg-Arg-Cys-Pro-Ala-Gln-Glu-Val-Ala-Arg-Gly-Val-Leu-Thr-Ser-Leu-Pro-Gly-Asp-Ser-Val-Thr-Leu-Thr-Cys-Pro-Gly-.

The present invention encompasses a polypeptide comprising the above sequence as well as any other polypeptide in which one or more amino acids in the structure of the IFN-β2/IL-6-R fragment are deleted or replaced with other amino acids, or one or more amino acids are added thereto, as long as they bind specifically IFN-β2/IL-6-R.

This invention also relates to a process for isolating IFN-β2/IL-6-R soluble extracellular fragment from a human fluid, e.g. urine, and its purification. In one preferred embodiment, the substantially purified receptor fragment of the invention is produced by a process which comprises:

a) recovering the crude protein fraction from a dialyzed concentrate of human urine of healthy donors b) subjecting said crude protein fraction of step (a) to affinity purification on a column of immobilized IFN-β2/IL-6;

c) applying said affinity purified active fractions of IFN-β2/IL-6 binding proteins from step (b) to reversed-phase HPLC; and d) recovering the fractions eluting at 39% acetonitrile and containing substantially purified IFN-β2/IL-6-R soluble extracellular fragment, said protein having a molecular weight of about 50K on SDS PAGE under non-reducing conditions and moving as a single peak on reversed-phase HPLC.

In a preferred embodiment, the crude protein fraction of step (a) is subjected first to ion exchange chromatography, .for example, on a carboxymethyl Sepharose (CM-Sepharose or CMS) column.

In another preferred embodiment, the affinity purification of step (b) is performed on a column of immobilized monoclonal antibodies raised against the IFN-β2/IL-6-R soluble fragment. The invention further relates to the preparation of IFN-β2/IL-6-R soluble extracellular fragment by genetic engineering techniques and encompasses all the tools used in these techniques. Thus the invention concerns DNA molecules comprising the nucleotide sequence coding for said receptor fragment or for a protein substantially homologous therewith. These DNA molecules may be genomic DNA, cDNA, synthetic DNA and combinations thereof.

The cloning of the IFN-β2/IL-6-R soluble extracellular fragment may be carried out by different techniques. The DNA coding for the fragment is synthesized or the gene coding therefor is isolated from a DNA library or the gene coding for the whole IFN-β2/IL-6 receptor is obtained first and then cut by known techniques. According to one approach, specific antibodies (polyclonal or monoclonal) to IFN-β2/IL-6 receptor are produced and used to search for cells producing the receptor by immunofluorescence or by Western blot. Then, mRNA is extracted from these IFN-β2/IL-6 receptor producing cells and is converted to cDNA by contacting with reverse transcriptase for a time and under conditions suitable to form said cDNA. The cDNA is cloned in an expression vector such as lambda gt 11, and screened by the use of the antibodies. The lambda gt 11 expression vector can be used for insertion of DNA up to 7 kb in length at a unique EcoRI site 53 bases upstream from the β-galactosidase termination codon. Therefore, foreign sequences DNA may be inserted into this site and expressed under appropriate conditions as fusion proteins. The lambda gt 11 expression vector is particularly useful for the construction of cDNA libraries to be screened with antibody probes (Huynh, T.V. et al. in: David Glover (ed.), *DNA Cloning Techniques: A Practical Approach*, IRL Press, Oxford (1984) pp. 49–78).

Following another approach, a synthetic oligonucleotide or a mixture of synthetic oligonucleotides, whose sequence is derived from the amino acid sequence of a fragment of the protein, e.g., the N-terminal amino acid sequence, are produced and used as probes for cloning the cDNA or the genomic DNA coding for the IFN-β2/IL-6 receptor or for its soluble fragment. Suitable DNA preparations, such as human genomic DNA, are enzymatically cleaved by restriction enzymes, or randomly sheared, and the fragments inserted into appropriate recombinant vectors to form a gene library. Such vectors can then be screened with synthetic oligonucleotide probes in order to identify a sequence coding for the IFN-β2/IL-6 receptor or for its soluble fragment.

Alternatively, the mRNA is isolated from cells which express the receptor and is converted, after purification, to cDNA as described above. The cDNA is converted to double-stranded cDNA by known techniques, is cloned and the resulting clones are screened with an appropriate probe for cDNA coding for the desired sequences. Once the desired clone is isolated, the cDNA is manipulated in substantially the same manner as the genomic DNA. However, with cDNA there will be no introns or intervening sequences.

The invention also relates to synthetic oligonucleotides to be used as probes to the DNA coding for IFN-β2/IL-6-R or for its soluble fragment. They are synthesized by known methods on the basis of the amino acid sequence of fragments of IFN-β2/IL-6-R. For this purpose, it is possible either to perform sequence analysis of the intact IFN-β2/IL-6-R or of its soluble extracellular fragment to obtain peptide fragments thereof and to characterize their amino acid sequence. The peptide fragments are obtained by subjecting purified protein preparations to fragmentation, e.g. by digestion with proteases such as trypsin, chymotrypsin or papain by methods well known in the art (Oike, Y. et al. (1982) J. Biol. Chem. 257:9751–9758), they are then separated by reverse-phase HPLC and sequenced by automatic amino acid sequencing techniques.

Once one or more suitable peptide fragments have been sequenced or a partial sequence of the protein is determined, the DNA sequences capable of encoding them are examined. Due to the degeneration of the genetic code, more than one codon may be used to encode a particular amino acid and one or more different oligonucleotides can be produced, each of which would be capable of encoding the IFN-β2/IL-6-R peptide fragments (Watson, J. D., in: *Molecular Biology of the Gene*, 3rd ed., W. A. Benjamin, Inc. Menlo Park, Calif. (1977), pp. 356–357). However, only one member of the set contains the nucleotide sequence that is identical to the nucleotide sequence of the gene. Its presence within the set and its capability to hybridize to DNA even in the presence of the other members of the set, makes it possible to employ the unfractionated set of oligonucleotides in the same manner in which one would employ a single oligonucleotide to clone the gene that encodes the peptide. The use of such oligonucleotide or set of oligonucleotides containing the theoretical "most probable" sequence capable of encoding the IFN-β2/IL-6-R gene fragments (following the "codon usage rules" disclosed by Lathe, R., et al. (1985) J. Molec. Biol. 183:1–12) permits to identify the sequence of a complementary oligonucleotide or set of oligonucleotides which is capable of hybridizing to the "most probable" sequence encoding the IFN-β2/IL-6-R or at least a portion thereof, or a set of such sequences. This oligonucleotide containing such a complementary sequence is then synthesized and employed as a probe to identify and isolate a DNA molecule coding for the IFN-β2/IL-6-R of the invention from a DNA library (Maniatis, T. et al. *Molecular Cloning: A Laboratory Manual*, Cold Spring Harbor Press, Cold Spring Harbor, N.Y. (1982).

In one of the embodiments, the isolation of the gene of the IFN-β2/IL-6 receptor is done by colony hybridization techniques under stringent conditions. Procedures for hybridization of nucleic acids are common knowledge and are disclosed, for example, in Maniatis, T., *Molecular Cloning A Laboratory Manual*, op. cit. and in Haymes, B. T., et al., *Nucleic Acid Hybridization: A Practical Approach*, IRL Press, Oxford, England (1985). By hybridization with the above nucleotide or set of oligonucleotides probes, it is possible to identify in a cDNA or genomic library, the DNA sequences capable of such hybridization and they are then analyzed to determine to what extent they contain encoding sequences for the IFN-β2/IL-6-R. The DNA coding for the receptor soluble extracellular fragment of the invention is then obtained from the DNA of positive clones of the whole receptor by known procedures and is inserted into appropriately constructed expression vectors by techniques well known in the art (see Maniatis et al., op cit.). Double-stranded cDNA is linked to plasmid vectors by homopolymeric tailing or by restriction linking involving the use of synthetic DNA linkers or blunt-ended ligation techniques. DNA ligases are used to ligate the DNA molecules and undesirable joining is avoided by treatment with alkaline phosphatase.

For expression of the desired protein, the expression vector should comprise also specific nucleotide sequences containing transcriptional and translational regulatory information linked to the DNA coding for the desired protein in such a way as to permit gene expression and production of the protein. First, in order for the gene to be transcribed, it must be preceded by a promoter recognizable by RNA polymerase, to which the polymerase binds and thus initiates the transcription process. There are a variety of such promoters in use, which work with different efficiencies (strong and weak promoters) and are different for prokaryotic and eukaryotic cells. High levels of gene expression in prokaryotic cells are achieved by using also ribosome-binding sites, such as the Shine-Dalgarno sequence (SD sequence). For eukaryotic hosts, different transcriptional and translational regulatory sequences may be employed, depending on the nature of the host. They may be derived from vital sources, such as adenovirus, bovine papilloma virus, Simian virus, or the like, where the regulatory signals are associated with a particular gene which has a high level of expression. Examples are the TK promoter of Herpes virus, the SV40 early promoter, the yeast gal4 gene promoter, etc. Transcriptional initiation regulatory signals may be selected which allow for repression and activation, so that expression of the genes can be modulated.

The DNA molecule comprising the nucleotide sequence coding for a protein comprising the amino acid sequence of the IFN-β2/IL-6-R soluble extracellular fragment of the invention, preceded by a nucleotide sequence of a signal peptide and the operably linked transcriptional and translational regulatory signals, is inserted into a vector which is capable of integrating the desired gene sequences into the host cell chromosome. The cells which have stably integrated the introduced DNA into their chromosomes can be selected by also introducing one or more markers which allow for selection of host cells which contain the expression vector.

In a preferred embodiment, the introduced DNA molecule will be incorporated into a plasmid or viral vector capable of autonomous replication in the recipient host. Prokaryotic and eukaryotic plasmids are well-known from the literature. Factors of importance in selecting a particular plasmid or viral vector include the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Once the vector or DNA sequence containing the construct(s) has been prepared for expression, the DNA construct(s) may be introduced into an appropriate host cell by any of a variety of suitable means: transformation, transfection, conjugation, protoplast fusion, electropotation, calcium phosphate-precipitation, direct microinjection, etc. Host cells to be used in this invention may be either prokaryotic or eukaryotic. Preferred prokaryotic hosts include bacteria such as *E. coli*, Bacillus, Streptomyces, Pseudomonas, Salmonella, Serratia, etc. The most preferred prokaryotic host is *E. coli*. Under such conditions, the protein will not be glycosylated. The prokaryotic host must be compatible with the replicon and control sequences in the expression plasmid. Preferred eukaryotic hosts are mammalian cells, e.g., human, monkey, mouse and chinese hamster ovary (CHO) cells, because they provide post-translational modifications to protein molecules, including correct folding or glycosylation at correct sites. Also yeast cells can carry out post-translational peptide modifications, including glycosylation.

After the introduction of the vector, the host cells are grown in a selective medium, which selects for the growth of vector- containing cells. Expression of the cloned gene sequence(s) results in the production of the desired IFN-β2/IL-6-R fragment. The expressed protein is then isolated and purified in accordance with the purification method described in the present application or by any other conventional procedure involving extraction, precipitation, chromatography, electrophoresis, or the like.

A further purification procedure that may be used in preference for purifying the protein of the invention is affinity chromatography using anti-IFN-β2/IL-6-R monoclonal antibodies, which are produced and immobilized on a gel matrix contained within a column. Impure preparations containing the recombinant protein are passed through the column. The protein will be bound to the column by the specific antibody while the impurities will pass through. After washing, the protein is eluted from the gel by a change in pH or ionic strength.

As used herein the term 'salts' refers to both salts of carboxyl groups and to acid addition salts of amino groups of the protein molecule formed by means known in the art. Salts of a carboxyl group include inorganic salts, for example, sodium, calcium, and salts with organic bases as those formed, for example, with amines, such as triethanolamine, arginine or lysine. Acid addition salts include, for example, salts with mineral acids and salts with organic acids.

"Functional derivatives" as used herein covers derivatives which may be prepared from the functional groups which occur as side chains on the residues or the N- or C- terminal groups, by means known in the art, and are included in the invention as long as they remain pharmaceutically acceptable, i.e. they do not destroy the activity of the protein and do not confer toxic properties on compositions containing it. These derivatives include aliphatic esters or amides of the carboxyl groups, and N-acyl derivatives of free amino groups or O-acyl derivatives of free hydroxyl groups formed with acyl moieties (e.g. alkanoyl or carbocyclic aroyl groups).

"Precursors" are compounds formed prior to, and converted into, IFN-β2/IL-6-R in the animal or human body. As "active fractions" of the substantially purified protein, the present invention covers any fragment or precursors of the polypeptide chain of the protein molecule alone or together with associated molecules or residues linked thereto, e.g. sugar or phosphate residues, or aggregates of the protein molecule or the sugar residues by themselves, provided said fraction has the ability to inhibit the cytotoxic effect of TNF on cells and/or to maintain its prolonged beneficial effect.

The invention further relates to antibodies against IFN-β2/IL-6-R and its soluble extracellular fragment and to F(ab) fragments thereof. The functional interaction of the antibodies of the present invention with IFN-β2/IL-6-R provides also a new diagnostic tool, based on immunoassays such as radioimmunoassay, ELISA etc., for the detection of over- or under-production of IFN-β2/IL-6-R by cells in the body in certain disorders.

The antibodies may be either polyclonal or monoclonal. They may be raised in rabbits, mice or other animals or tissue cultured cells derived thereof or can be products of cells of human origin. They may also be produced by recombinant DNA technology either in a form identical to that of the native antibody or as chimeric molecules, constructed by recombination of antibody molecules of man and animal origins. The development of antibody level is followed by the ability of the animal serum to inhibit the hybridoma growth factor (HGF) activity of IFN-β2/IL-6.

For the preparation of the antibodies, either purified IFN-β2/IL-6 receptor or its soluble extracellular fragment or one or more synthetic peptides identical to the known sequence of the proteins, e.g. to the N-terminal protein sequence, may be used to immunize animals. A further possibility is to fuse one of the possible nucleotide sequences coding for a fragment of the receptor to the gene coding for Protein A, to express the fused Protein A-IFN-β2/IL-6-R gene in $E.$ $coli$, to purify the fused protein by affinity chromatography on IgG Sepharose column and then to use it to immunize animals.

The monoclonal antibodies of the present invention are prepared using conventional hybridoma technique (Kohler et al. (1975) Nature 256:495; Kohler et al. (1976) Eur. J. Immunol. 6:511). After immunization, spleen cells alone and/or together with lymph node cells of the immunized animals are isolated and fused with a suitable myeloma cell line. After fusion, the resulting hybridoma cells are selectively maintained in HAT medium and then cloned. The hybridoma cells obtained through such a selection are then asseyed to identify clones which secrete antibodies capable of binding IFN-β2/IL-6 receptor or its soluble extracellular fragment. After identification, the desired clones are grown in bulk, either in suspension culture or in ascitic fluid, by injecting the cells into the peritoneum of suitable host mice. The monoclonal antibodies produced by the hybridomas are then isolated and purified.

As mentioned before, the monoclonal antibodies may also be immobilized and used for the purification of the IFN-β2/IL-6 receptor or its soluble extracellular fragment in affinity purification procedure using an immunoadsorbent column.

The IFN-β2/IL-6-R and its soluble extracellular fragment axed salts, functional derivatives, precursors and active fractions thereof, and mixtures of any of the foregoing, are indicated for stimulating and enhancing the desirable effects of IFN-β2/IL-6 in mammals, such as the antiproliferative activity of IFN-β2/IL-6.

The present invention further relates to pharmaceutical compositions comprising a pharmaceutically acceptable carrier, IFN-β2/IL-6 and the IFN-β2/IL-6-R, its soluble extracellular fragment or salts, functional derivatives, precursors or active fractions thereof, and mixtures of any of the foregoing, as active ingredients. These compositions may be used in any condition where it is desired to stimulate the activity of IL-6. Of course the amount of IFN-β2/IL-6 to be administered is lower in view of the enhancing effect of the receptor. The way of administration can be via any of the accepted modes of administration for similar agents and will depend on the condition to be treated.

The pharmaceutical compositions of the invention are prepared for administration by mixing the active ingredients with physiologically acceptable carriers, stabilizers and excipients, and prepared in dosage form, e.g. by lyophilization in dosage vials. The amount of active compounds to be administered will depend on the route of administration, the disease to be treated and the condition of the patient.

The IFN-β2/IL-6-R and its soluble extracellular fragment and salts, functional derivatives, precursors and active fractions thereof, and mixtures of any of the foregoing, may also be used alone for enhancing the activity of endogenously formed IFN-β2/IL-6 in conditions like bacterial infections, burns, trauma, etc.

The invention will now be illustrated by the following non-limiting examples:

EXAMPLE 1

Isolation and purification of IFN-β2/IL-6 receptor from human placenta

Placental membranes are prepared according to the method of R. A. Hock and M. D. Holleneberg (1980), J. Biol. Chem., 255, 10731–10736, as follows: placenta pieces are homogenized in a buffer consisting of 25 mM Tris-HCl, pH 7.4, 0.25M sucrose, 0.1M NaCl, 1.5 mM MgCl$_2$, 2 mM EGTA, 1 mM PMSF and 22 Tiu/ml Aprotinin, followed by filtering through gauze and centrifugation (10,000×g for 30 min. at 4° C.). NaCl and MgSO$_4$ are added to the supernatant to a final concentration of 0.1M and 0.2 mM respectively. The mixture is spun (48,000×g for 40 min. at 4° C.) and the resulting pellet is resuspended in a buffer of 10 mM Hepes, pH 7.4, 150 mM NaCl and 1 mM PMSF and 22 Tiu/ml. The membranes are then solubilized in a solubilization buffer (final concentrations: 10 mM Hepes, pH 7.4, 1–2% Triton X-100, 1 mM PMSF and 20 units/ml aprotinin). The suspension is spun first at 10,000×g for 15 min. and then at 100,000×g for 60 min. The supernatant is applied to an immobilized IFN-β2/IL-6 column (2,5 mg per 0.8 ml of Affigel-10). Loading is at a flow rate of 0.2–0.5 ml/min. The column is then washed with PBS (50 ml) and the bound material is eluted with a solution of 25 mM citric acid. Fractions of 1 ml are collected and immediately neutralized with 1M Hepes, pH 8.5. Each fraction is tested for its ability to bind $^{125}$I-IFN-β2/IL-6 and for protein content. Protein is determined with fluorescamine.

EXAMPLE 2

Isolation and purification of IFN-β2/IL-6-R soluble extracellular fragment 2.1 Preparation of the urine concentrate A pool of 200 liter urine from healthy menopausal women was subjected to microfiltration on a Pollicon membrane with a pore size of 0.45 μm. The filtrate was concentrated by ultrafiltration using a Pellicon membrane with a molecular weight cut off of 10K to a final volume of 500 ml. The concentrate was dialyzed against phosphate buffered saline containing 1 mM benzamidine and 0.1% sodium azide.

2.2 Ion-exchange chromatography on CM-Sepharose

A CM-Sepharose (Pharmacia, Uppsala, Sweden) cation exchange column (2.7×10 cm) was prewashed with 1M NaCl, 10 mM citric acid pH 5.0, containing 0.02% NaN$_3$ (buffer C) and equilibrated with 10 mM citric acid (pH 5) containing 0.02% NaN$_3$ (buffer A). The concentrate of urinary proteins was dialyzed against buffer A, and centrifuged for 15 min. at 8000×g. The supernatant was applied at 4° C. on the column at a flow rate of 2 ml/min. The column was washed with 1500 ml buffer A and eluted with 250 ml of a solution containing 200 mM NaCl, 10 mM citric acid (pH 5.0) and 0.02% NaN$_3$ (buffer B). A second step of elution was performed with 150 ml buffer C. Fractions of 50 ml were collected and tested for IFN-β2/IL-6 binding activity (binding of $^{125}$I-IFN-β2/IL-6) and their protein concentration was determined.

2.3 Affinity purification on an IFN-β2/IL-6 column

IFN-β2/IL-6 was brought to a concentration of 5 mg/ml, then equilibrated with PBS containing 0.02% sodium azide and coupled to Affigel-10 (2.5 mg to 0.8 ml beads). The concentrate of urinary proteins of step 2.1 or 2.2 was equilibrated with phosphate-buffered saline (PBS) and applied to the IFN-β2/ IL-6 Affigel-10 column (2.5 mg of protein bound to 0.8 ml of Affigel-10) at a flow rate of 0.2 ml/min. at 4° C. Unbound proteins were washed with PBS and the bound proteins were then eluted at pH 2.5 by applying a solution of 25 mM citric acid, 1 ml fractions were collected into tubes containing 1M Hepes pH 8.5. The eluted protein was monitored for protein and for binding of $^{125}$I-IFN-β2/IL-6 following electroblotting.

2.4 Reversed-phase high pressure liquid chromatography

Figure 1:
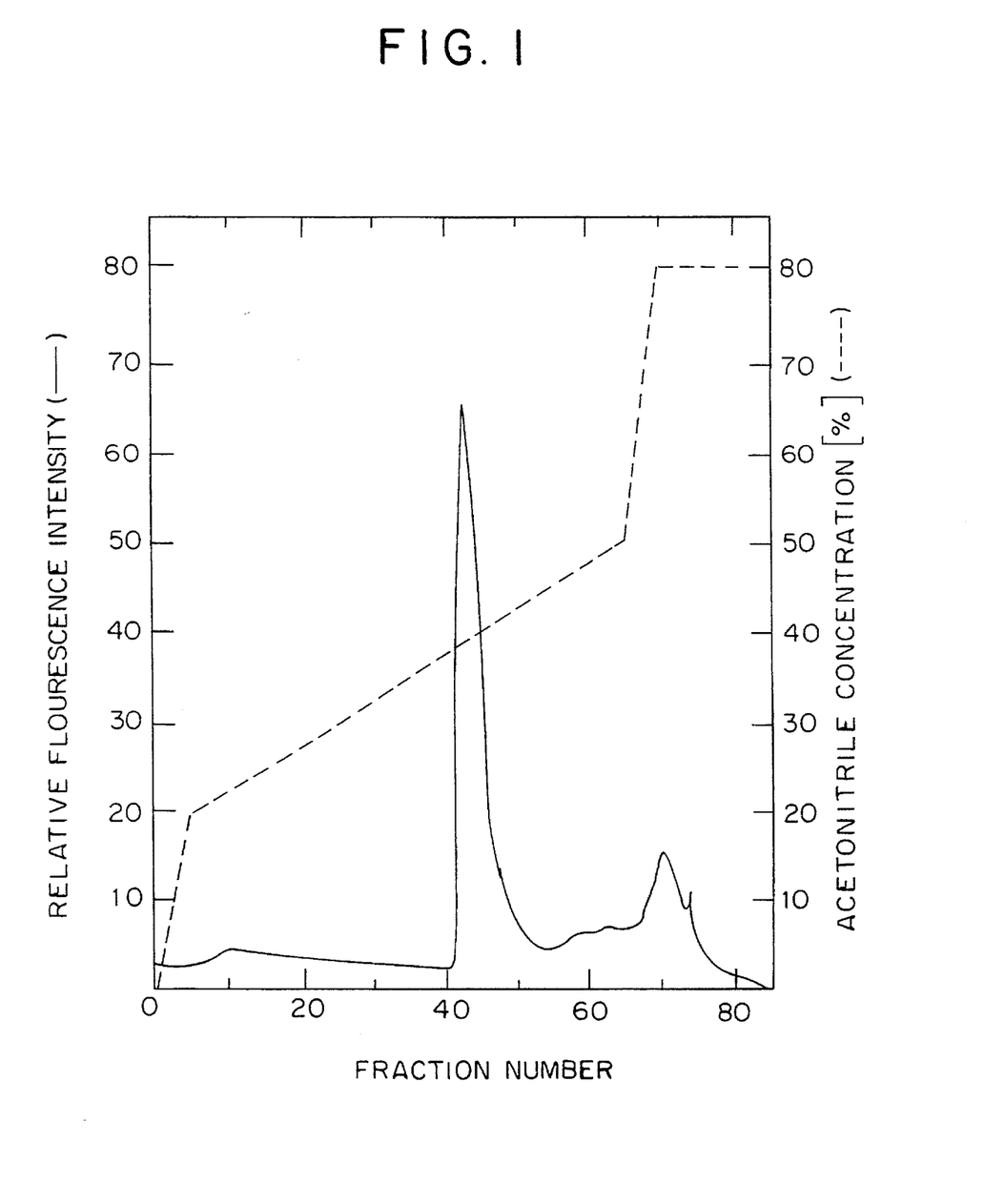
FIG. 1 shows the reversed-phase HPLC column elution pattern of IFN-β2/ IL-6-R soluble extracellular fragment fractions after partial purification on an immobilized IFN-β2/IL-6 column.

The reversed-phase HPLC column Aquapore RP-300 4.6×30 mm (Brownlee Labs) was prewashed with 0.3% aqueous trifluoroacetic acid (TFA) (Buffer F) until a stable baseline was obtained by the fluorescamine detection system. The protein peak fractions eluted from the affinity IFN-β2/IL-6 columns of step 2.3 were pooled and injected in one 1.8 ml portion onto the column. The column was run with Buffer F at a flow rate of 0.5 ml/minute until the fluorometer did not detect any protein. Elution was performed at a flow rate of 0.5 ml/minute, with a linear gradient of acetonitrile in Buffer F (----) (0–20% for 5 minutes, followed by 20–50% for 60 minutes, and finally 50–80% for 5 minutes). The column was then washed for 15 minutes with 80% acetonitrile. Fractions of 0.5 ml were collected and tested for protein content (—) and for binding of $^{125}$I-IFN-β2/IL-6 following electroblotting. As shown in FIG. 1, the active proteins were found to elute as one protein peak, in fractions corresponding to about 39% acetonitrile.

2.5 SDS-PAGE and binding to $^{125}$I-IFN-β2/IL-6

Figure 2:
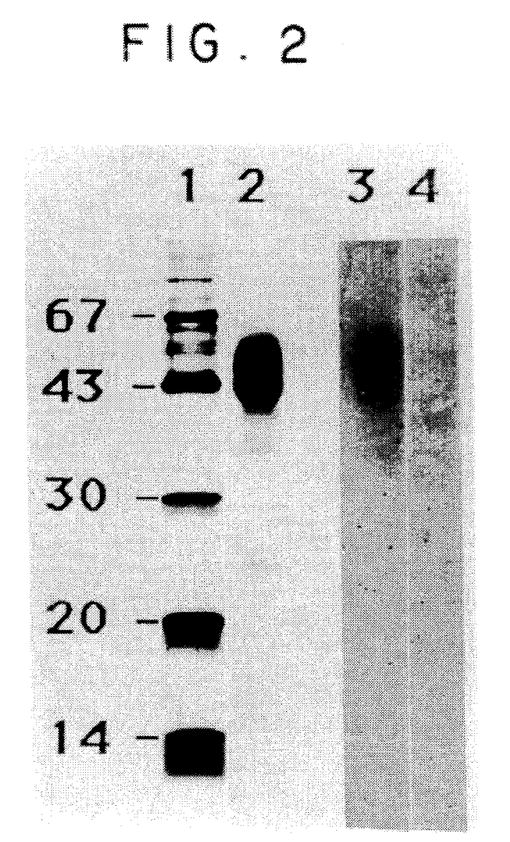
FIG. 2 shows the results of analysis of the purified IFN-β2/IL-6-R soluble extracellular fragment fraction by SDS-PAGE under non-reducing conditions, followed by silver staining (lanes 1 and 2), or followed by electroblotting, $^{125}$I-rIFN-β2/IL-6 binding, and visualization by autoradiography (lanes 3 and 4).

In order to monitor the result of the purification, sodium dodecyl sulphate polyacrylamide gel electrophoresis (SDS-PAGE) was performed under non-reducing conditions according to the method of Laemmli U. K. et al. (Nature (1970) 227:680). Samples of the active fractions eluting from the reversed-phase HPLC, were mixed with 3×concentrated sample buffer containing no SDS and no β-mercaptoethanol and loaded on a 12% acrylamide gel. In FIG. 2, as a reference for molecular weight, a mixture of molecular weight markers (α lactalbumin 14.4K, soya bean trypsin inhibitor 20.1K, carbonic anhydrase 30K, ovalbumin 43K, bovine serum albumin 67K, and phosphorylase b. 94K) was loaded on lane 1. The gel was run at 150 volt and the protein bands were visualized by silver staining (Oakley, B. R. et al. Anal. Biochem. 105:361). In lane 2, it is shown that the HPLC-purified IFN-β2/IL-6 binding protein moved as a single band, with an apparent molecular weight of 50 (40–60)K. Binding of $^{125}$I-IFN-β2/IL-6 (2.2×10$^7$ cpm/μg, 1.5×10$^6$ cpm/ml) was done following SDS-PAGE under non-reducing conditions and electroblotting onto nitrocellulose membrane (Schleicher and Schuell 0.45 μm), performed essentially as the Western blotting method (Towbin, H. et al., Proc. Natl. Acad. Sci. USA, 76, 4350–4354, 1979). As shown in lane 3, only the 50 (40–60)K protein of the partially purified protein sample from the IFN-β2/ IL-6 affinity column eluate reacted specifically with $^{125}$I-IFN-β2/IL-6. A purified IFN-gamma binding protein sample from IFN-gamma affinity column eluate was used as a negative control (lane 4). Lanes 3 and 4 were visualized by autoradiography.

2.6 N-Terminal Sequence Analysis

Samples of the substantially purified IFN-β2/IL-6-R soluble extracellular fragment of the invention (1–5 μg, 50–200 pmol each) were applied to pretreated, biobrene-coated glass-fiber discs. The dried discs were subjected to repetitive cycles of Edman degradation in an automated pulsed liquid gas phase protein microsequencer (Model 475) with an on-line HPLC PTH-amino acid analyzer (Model 120) and a data acquisition and processing unit Model 900, (all from Applied Biosystems Inc. Foster City, Calif., U.S.A.). The computer-derived sequence was compared with the raw data and was corrected when necessary. Altogether two separate analyses were performed in order to confirm the sequence data. The initial yield was over 40%, indicating that the major protein in the preparation (the 50K band) is related to the resulting sequence. The N-terminal sequencing of this soluble extracellular fragment of the IFN-β2/IL-6-R gave the following amino acid sequence:

Leu-Ala-Pro-Arg-Arg-Cys-Pro-Ala-Gln-Glu-Val-Ala-Arg-GlY-Val-Leu-Thr-Ser-Leu-Pro-Gly-Asp-Ser-Val-Thr-Leu-Thr-CYs-Pro-Gly-

EXAMPLE 3

Preparation of polyclonal antibodies to IFN-β2/IL-6-R

Rabbits were initially injected subcutaneously with 10 μg of a pure preparation of the IFN-β2/IL-6-R soluble extracellular fragment emulsified in complete Freund's adjuvant. Three weeks later they were injected again subcutaneously with 10 μg of the preparation in incomplete Freund's adjuvant. Three additional injections as solution in PBS were given at 10 day intervals. The rabbits were bled 10 days after the last immunization. The development of antibody level was followed by the ability of the rabbit serum to inhibit the HGF (hybridoma growth factor) activity of IFN-β2/IL-6. The immunoglobulins of the rabbit sera were precipitated by the addition of ammonium sulfate and centrifugation, and purified by dialysis and chromatography.

EXAMPLE 4

Preparation of monoclonal antibodies to IFN-β2/ILN-6-R

Female Balb/C mice (3 months old) were first injected with 2.5 μg purified IFN-β2/IL-6-R soluble extracellular fragment in an emulsion of complete Freund's adjuvant, and three weeks later, subcutaneously in incomplete Freund's adjuvant. Three additional injections were given at 10 day intervals, subcutaneously in PBS. A final boost was given intraperitoneally 3 days before the fusion to the mouse showing the highest binding titer in inverted solid phase RIA. Fusion was performed using NSO/1 myeloma cell line and lymphocytes prepared from both the spleen and lymph nodes of the animal as fusion partners. The fused cells were distributed into microculture plates and the hybridomas were selected in DMEM supplemented with HAT and 15% horse serum. Hybridomas that were found to produce antibodies to IFN-β2/IL-6-R were subcloned by the limiting dilution method and injected into Balb/C mice that had been primed with pristane for the production of ascites. Immunoglobulins were isolated from the ascites by ammonium sulfate precipitation (50% saturation), centrifuged, redissolved in water and dialyzed against PBS containing 0.02% azide. The isotypes of the antibodies were defined either with the use of a commercially available ELISA kit (Amersham, U. K.), or by the Ouchterlony method using commercially available antisera against different isotypes.

The screening of the anti-IFN-β2/IL-6-R monoclonal antibodies producing hybridomas was performed as follows: Hybridoma supernatants were tested for the presence of anti-IFN-β2/IL-6-R antibodies by an inverted solid phase radioimmunoassay (iRIA). PVC microtiter plates (Dynatech Laboratories, Alexandria, Va.) were coated with affinity purified goat anti-mouse serum F(ab)$_2$ antibodies (BioMakor) (10 μg/ml, 80 μl/well). Following overnight incubation at 4° C. the plates were washed twice with PBS containing BSA (0.5%) and Tween 20 (0.05%) and blocked in washing solution for at least 2 hrs at 37° C. Hybridoma culture supernatants (50 μl/well) were added and the plates were incubated for 4 hrs at 37° C. The plates were then washed three times with the washing solution and $^{125}$I-IFN-β2/IL-6-R (50 μl, 10$^5$ cpm) was added for further incubation of 16 hrs at 4° C. The plates were washed 3 times and individual wells were cut and counted in a gamma counter. Samples giving counts that were at least 5 times higher than the negative control value were considered positive (Table I). Thirty positive clones were selected, subcloned for further studies and characterized.

EXAMPLE 5

Western blotting

Western blotting was performed as follows: Samples of partially purified IFN-β2/IL-6-R soluble fragment from human urine were analyzed by SDS PAGE under reducing conditions and electroblotted onto nitrocellulose sheets (BA85, Schleicher and Shuell). Following electroblotting the sheet was incubated overnight with a blocking buffer (5% non-fat milk in PBS containing 0.05% Tween 20 and 0.02% sodium azide) and then for 2 hrs at room temperature with the anti-IFN-β2/IL-6-R monoclonal antibody No. 34-4. Following washing in 0.05% Tween 20 in PBS, other nitrocellulose was incubated for 4 hrs at room temperature with $^{125}$I-goat anti-mouse serum (0.7×10$^6$ cpm/ml in the blocking buffer). The sheet was then washed, dried and autoradiographed.

Some of the isolated clones and subclones with their isotype and results of binding of IFN-β2/IL-6-R in inverted RIA and Western blotting are listed in Table I.

TABLE I

Clones producing monoclonal antibodies to IFN-β2/IL-6 receptor

| Clone number | Screening with iRIA [CPM] | Western blot +M* | Western blot −M | Isotype |
|---|---|---|---|---|
| 4.4 | 20,455 | + | + | IgG$_1$ |
| 5 | 1,085 | + | + | IgM |
| 17.1 | 36,565 | + |   | IgG$_{2a}$ |
| 20.2 | 31,450 | + |   | IgG$_1$ |
| 22 | 11,465 | + | + | IgG$_2$ |
| 24.2 | 8,850 | + | + | IgG$_1$ |
| 25 | 2,000 |   |   | IgG$_{2a}$ |
| 28.7 | 1,645 |   |   | IgG$_1$ |
| 29 | 4,165 |   |   |   |
| 30.8 | 1,755 | + |   | IgM |
| 31 | 3,060 |   |   |   |
| 32.5 | 31,465 | + | + | IgG$_1$ |
| 33.2 | 14,875 |   |   | IgG$_1$ |
| 34.4 | 33,480 | + |   | k,IgG$_1$ |
| 35.2 | 35,495 | + | + | k,IgG$_3$ |
| 36 | 1,445 | + |   | IgM |
| 37 | 9,640 |   |   | IgG$_1$ |
| 38.4 | 35,975 | + |   | IgG$_1$ |
| 39.1 | 5,195 | + | + | IgG$_2$ |
| 40 | 1,415 | + |   | IgG$_1$ |
| 41 | 1,870 | + |   | IgG$_1$ |
| 42.5 | 33,565 |   |   | IgG$_1$ |
| 43 | 1,255 |   |   | IgG$_1$ |
| 46 | 6,090 |   |   |   |
| 48 | 18,000 |   |   | IgG$_1$ |
| 49 | 8,000 | + |   | IgM |
| 50.3 | 28,440 | + | + | IgG$_1$ |
| 51 | 1,075 |   |   | IgG$_1$ |
| 52 | 3,945 |   |   | IgM |
| 53.4 | 3,440 |   |   | IgG$_1$ |

*M: mercaptoethanol (reducing agent)

EXAMPLE 6

Affinity chromatography of IFN-β2/IL-6-R soluble fragment preparations with monoclonal antibodies Antibodies against IFN-β2/IL-6-R are utilized for the purification of the soluble fragment by affinity chromatography. The monoclonal antibody No. 34-4 was used in this example for affinity chromatography, after testing its binding capacity for the radiolabeled antigen in inverted solid phase radioimmunoassay (iRIA). Ascitic fluid containing the monoclonal antibody secreted by hybridoma No. 34-4 was purified by ammonium sulfate precipitation at 50% saturation followed by extensive dialysis against PBS. About 10 mg of immunoglobulins were bound to 1 ml polyacrylhydrazide agarose as specified by Wilchek and Miron, *Methods in Enzymology* 34:72–76, 1979. 250 ml of human urine, partially purified on carboxymethyl sepharose (CMS) column (equivalent to 250 l of crude urine) were loaded on 0.5 ml of the anti-IFN-β2/IL-6-R antibody column at 4° C. at a flow rate of 0.25 ml/min. The column was washed with PBS until no protein was detected in the washings. IFN-β2/IL-6-R soluble fragment was eluted by 25 mM citric acid buffer, pH 2.2 (8×1 column volume fractions) and immediately neutralized by 1M Hepes buffer, pH 8.5, with a total recovery of 88% IFN-β2/IL-6-R soluble fragment. Silver stain analysis of SDS PAGE of the eluted fractions revealed a major band of M.W. of 50,000 and another major band of 150,000 (contaminants). Further purification of this preparation was obtained by RP-300 HPLC, and the soluble receptor fragment eluted at 39% acetonitrile in a pattern similar to that of FIG. 1.

TABLE II

| | Immunoaffinity purification of IL-6 receptor from urine (CMS) | | | | | | |
|---|---|---|---|---|---|---|---|
| McAb | | FLUORESCAMINE | | | ELISA | | |
| column | Sample | ml | µg/ml | µg | µg/ml | µg | purity % | yield % |
| 34.4 | Load | 250 | 2200 | 550,000 | 0.38 | 95 | | |
| | Efluent | 250 | 2000 | 500,000 | 0.06 | 15 | | |
| | Elution 1 | 1.2 | 20 | 24 | 7.7 | 9 | 38 | |
| | Elution 2 | 1.2 | 45 | 54 | 30.4 | 36.5 | 67 | |
| | Elution 3 | 1.2 | 18 | 21.6 | 12 | 14.4 | 80 | |
| | Elution 4 | 1.2 | 11 | 13 | 8 | 9.6 | 87 | |
| | Total eluted | | | | | 69.5 | | 88 |

EXAMPLE 7

ELISA test

Microtiter plates (Dynatech or Maxisorb by Nunc) were coated with anti-IFN-β2/IL-6-R monoclonal antibody No. 34-4 (immunoglobulin fraction, 120 µl, 20 µg/ml in PBS), overnight at 4° C. The plates were washed with PBS containing BSA (0.5%) and Tween 20 (0.05%) and blocked in the same solution for at least 2 hrs at 37° C. The tested samples were diluted in the blocking solution and added to the wells (100 µl/well) for 4 hrs at 37° C. The plates were then washed 3 times with PBS containing Tween 20 (0.05%) followed by the addition of rabbit antI-IFN-β2/IL-6-R serum (1:1000, 100 µl/well) for further incubation of 4 hrs at 37° C. The plates were washed 3 times and a conjugate of goat-anti-rabbit horseradish peroxIdase (HRP, BioMakor, 1:2000, 100 µl/well) was added for 2 hrs at 37° C. The plates were washed 4 times and the color was developed by ABTS (2,2'-azino-bus(3-ethylbenzthiazoline-6-sulfonic acid), Sigma) substrate. The plates were read by an automatic ELISA reader. Alternatively, the ELISA could be performed by replacing the rabbit polyclonal anti-IFN-β2/IL-6-R antibodies with a monoclonal antibody No. 22-1 either conjugated to HRP or biotinylated.

EXAMPLE 8

The activity of the IFN-β2/IL-6-R soluble extracellular fragment was tested on the hybridoma/plasmacytoma growth factor (HGF) activity of IFN-β2/IL-6. Murine plasmacytoma T1165 cells were exposed for 16 hours to a low concentration of pure human recombinant IFN-β2/IL-6, produced in E.coli and purified to homogeneity ($2 \times 10^6$ HGF units/mg). In parallel, the same IFN-β2/IL-6 samples were incubated for 90 minutes at 37° C. with various concentrations of the IFN-β2/IL-6-R soluble extracellular fragment and then added to the cells. With 0.25 ng/ml IFN-β2/IL-6 alone, there was no stimulation of $^3$H-thymidine incorporation in the pulsed T1165 cells, but addition of IFN-β2/IL-6-R soluble extracellular fragment produced a dose-dependent stimulation (Table III). At 5 ng/ml IFN-β2/IL-6, growth stimulation of the T1165 cells was seen and only slightly stimulated by IFN-β2/IL-6-R soluble extracellular fragment. As a control, the IFN-gamma soluble receptor purified from human urine had no effect (Table III).

Subliminal concentrations of IFN-β2/IL-6 can, therefore, be specifically potentiated by addition of IFN-β2/IL-6-R soluble extracellular fragment. Assuming about 5,000 IFN-β2/IL-6 receptors on the cells, 0.25 ng/ml IFN-β2/IL-6 corresponds to about 150 molecules of the cytokine per receptor. The stimulatory effect of IFN-β2/IL-6-R soluble extracellular fragment begins to be seen when 5–10,000 IFN-β2/IL-6-R soluble extracellular fragment molecules are added per murine IFN-β2/IL-6 receptor. Although part of the IFN-β2/IL-6-R soluble extracellular fragment may be inactive, it does not appear that the effect is stochiometric.

Several lines of human B-cells transformed by Epstein-Barr virus (EBV) show growth stimulation by IFN-β2/IL-6. In the TI cell line, addition of IFN-β2/IL-6-R soluble extracellular fragment did not potentiate the effect of IFN-β2/IL-6 as it did on the murine T1165 plasmacytoma (Table IV). In fact, with the TI cells, IFN-β2/IL-6-R soluble extracellular fragment behaved as an inhibitor of IFN-β2/IL-6 action at low concentrations of the cytokine.

In the HGF activity assay the bioactivity of the IFN-β2/IL-6 is measured by stimulation of $^3$H-thymidine incorporation in murine plasmacytoma T1165 cells (Nordan, R. P. and Potter, M. Science (1986) 233:566–568). Briefly, serial dilutions (60 µl) of the tested samples were incubated with T1165 cells ($10^4$ cells in 40 µl) overnight at 37° C. in 96-well microtiter plates. A pulse of $^3$H-thymidine (1 µCi/well) was given for 4 hrs at 37° C. Cells were harvested by an automatic harvester and counted. One unit of IFN-β2/IL-6 is defined as the amount of protein that gives 50% of the maximal effect in the assay.

TABLE III

| Stimulation of mouse plasmacytoma T1165 cell growth | | |
|---|---|---|
| IFN-β2/IL-6 ng/ml | IFN-β2/IL-6-R soluble extracellular fragment | $^3$H-thymidine incorporation counts per minute |
| None | None | 5,800 |
| 0.25 | None | 5,780 |
| " | 0.03 | 7,750 |
| " | 0.06 | 9,100 |
| " | 0.12 | 10,100 |
| " | 0.25 | 20,000 |
| " | 0.50 | 29,750 |
| " | 1.00 | 40,400 |
| 2.5 | None | 16,000 |
| 2.5 | 0.25 | 16,000 |
| 5.0 | None | 32,000 |
| 5.0 | 0.25 | 48,000 |
| 0.25 | IFN-γ-R soluble fragment | 6,350 |

TABLE IV

Stimulation of human EBV-transformed B-cell line TI

| IFN-β2/IL-6 ng/ml | ³H-thymidine incorporation counts per minute × 10⁻³ | |
|---|---|---|
| | Alone | +IFN-β2/IL-6-R soluble extracellular fragment |
| None | 20 | 25 |
| 0.05 | 33 | 25 |
| 0.2 | 39 | 29 |
| 12.5 | 39 | 40 |
| 25.0 | 42 | 39 |

The IFN-β2/IL-6-R soluble extracellular fragment concentration was 0.6 μg/ml.

EXAMPLE 9

Activity on human breast cancer cells

Human breast ductal carcinoma cells T47D are growth-inhibited by IFN-β2/IL-6. These cells are rich in IFN-β2/IL-6 receptor binding sites, at least comparable to what is found on lymphocytes and myeloid cells. A series of subclones of the T47D cancer cell culture were isolated and compared for their growth inhibition by IFN-β2/IL-6. By several tests, colony formation from sparsely seeded cells and ³H-thymidine incorporation in semi-confluent monolayers, some clones (e.g. 07) were more sensitive and others (e.g. 012) were less sensitive than the parental T47D cultures. The effect of IFN-β2/ IL-6-R soluble extracellular fragment was tested in an ³H-thymidine incorporation assay where IFN-β2/IL-6 produces a dose-dependent inhibition (Table V).

Figure 3:
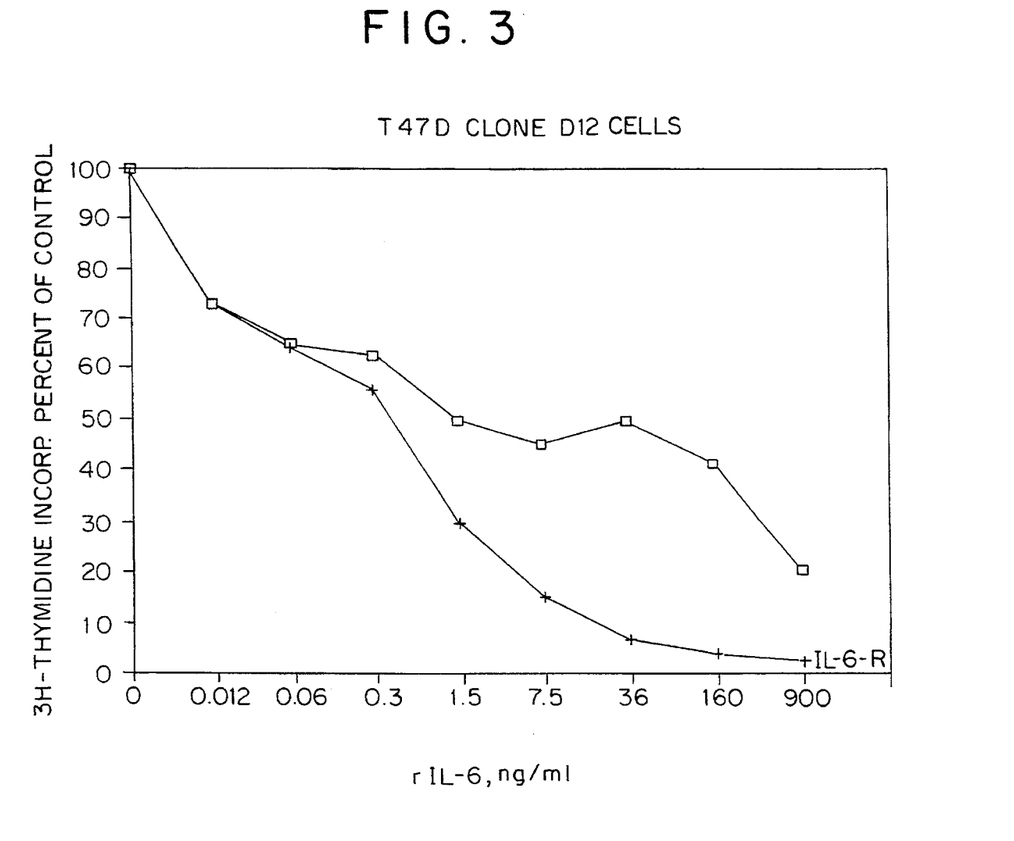
FIG. 3 shows the enhancement of IFN-β2/IL-6 HGF activity by IFN-β2/IL-6-R soluble extracellular fragment on human breast carcinoma T47D cells.

Whereas addition of IFN-β2/IL-6-R soluble extracellular fragment alone had no effect, the soluble receptor strongly increased the antigrowth effect of IFN-β2/IL-6 (Table V). Unlike what was found on the murine plasmacytoma cells, the effect of IFN-β2/IL-6-R soluble extracellular fragment on the human breast cancer cells was marked at higher IFN-β2/IL-6 concentrations. There was not only a reduction in the amount of IFN-β2/IL-6 needed for 50 percent inhibition, but the amplitude of the effect was markedly increased. In the presence of IFN-β2/IL-6-R soluble extracellular fragment, the inhibition of ³H-thymidine incorporation reached 98 percent, while without IFN-β2/IL-6-R soluble extracellular fragment residual DNA synthesis was observed even at high IFN-β2/IL-6 doses. This result suggested that IFN-β2/ IL-6-R soluble extracellular fragment may also make a more resistant subclone such as 012 respond fully to IFN-β2/IL-6 growth inhibition. Indeed, addition of IFN-β2/IL-6-R soluble extracellular fragment, allowed also to inhibit almost completely the ³H-thymidine incorporation in 012 cells (FIG. 3) and the effect was again evident at the higher IFN-β2/IL-6 concentrations.

These results show that IFN-β2/IL-6-R soluble extracellular fragment acts on human breast cancer cells and increases both the sensitivity and the amplitude of the response.

TABLE V

Inhibition of Human Breast Carcinoma T47D clone 07 growth

| IFN-β2/IL-6 ng/ml | ³H-thymidine incorporation counts per minute × 10⁻³ | |
|---|---|---|
| | Alone | +IFN-β2/IL-6-R soluble extracellular fragment |
| None | 100 | 103 |
| br 1.5 | 57 | 32 |
| 7.5 | 46 | 12 |
| 36 | 37 | 4 |
| 180 | 26 | 2 |
| 900 | 12 | 4 |

The IFN-β2/IL-6-R soluble extracellular fragment concentration was 0.6 μg/ml.

We claim:

1. Substantially purified protein having the same amino acid sequence as human interferon-β2/interleukin-6 receptor (IFN-β2/IL-6-R) soluble extracellular fragment, isolatable from human urine, having an apparent molecular weight of about 40–60K when analyzed by SDS-PAGE under non-reducing conditions, moving as a single peak on reversed-phase high performance liquid chromatography (HPLC), and containing the following N-terminal amino acid sequence:

Leu-Ala-Pro-Arg-Arg-Cys-Pro-Ala-Gln-Glu-Val-Ala-Arg-Gly-Val-Leu-Thr-Ser-Leu-Pro-Gly-Asp-Ser-Val-Thr-Leu-Thr-Cys-Pro-Gly-.

2. A protein in accordance with claim 1, comprising a recombinant protein.

* * * * *